(12) United States Patent
Solis et al.

(10) Patent No.: US 10,357,173 B2
(45) Date of Patent: Jul. 23, 2019

(54) DUAL MULTIRAY ELECTRODE CATHETER

(71) Applicant: Biosense Webster (Israel) Ltd., Yokneam (IL)

(72) Inventors: Mario A. Solis, Rancho Cucamonga, CA (US); Shubhayu Basu, Anaheim, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 326 days.

(21) Appl. No.: 14/853,653

(22) Filed: Sep. 14, 2015

(65) Prior Publication Data

US 2017/0071494 A1    Mar. 16, 2017

(51) Int. Cl.
| | | |
|---|---|---|
| *A61B 5/042* | (2006.01) | |
| *A61B 18/14* | (2006.01) | |
| *A61B 5/00* | (2006.01) | |
| *A61B 18/00* | (2006.01) | |

(52) U.S. Cl.
CPC .......... *A61B 5/0422* (2013.01); *A61B 5/6859* (2013.01); *A61B 18/1492* (2013.01); *A61B 2018/00267* (2013.01); *A61B 2018/00357* (2013.01); *A61B 2018/00577* (2013.01)

(58) Field of Classification Search
CPC ............................. A61B 5/0422; A61B 5/6859
See application file for complete search history.

(56) References Cited

U.S. PATENT DOCUMENTS

| | | |
|---|---|---|
| 5,239,724 A | 8/1993 | Salecker et al. |
| 5,332,089 A | 7/1994 | Tillett et al. |
| 5,391,199 A | 2/1995 | Ben-Haim |
| 5,484,118 A | 1/1996 | Fujimura et al. |
| 5,618,612 A | 4/1997 | Gstrein |
| 5,672,174 A | 9/1997 | Gough et al. |
| 5,690,963 A | 11/1997 | Spargo et al. |
| 5,772,590 A | 6/1998 | Webster, Jr. |
| 5,855,576 A * | 1/1999 | LeVeen .............. A61B 18/1477 606/41 |
| 5,855,592 A * | 1/1999 | McGee ................ A61N 1/3918 600/374 |

(Continued)

FOREIGN PATENT DOCUMENTS

| | | |
|---|---|---|
| EP | 2752153 A1 | 7/2014 |
| EP | 2842604 A1 | 4/2015 |
| WO | 96/05768 | 2/1996 |

OTHER PUBLICATIONS

U.S. Appl. No. 13/860,921.

(Continued)

*Primary Examiner* — Lee S Cohen
(74) *Attorney, Agent, or Firm* — Dergosits & Noah LLP; Todd A. Noah

(57) ABSTRACT

This disclosure is directed to a catheter having a dual multiray electrode assembly at the distal end of the catheter body formed from a plurality of spines with electrodes and a dual multiray electrode assembly at the distal end of the catheter body. The dual multiray electrode assembly may have a proximal multiray array and a distal multiray array, each array comprising a plurality of spines connected at one end. The dual multiray electrode assembly may have an expanded configuration and a collapsed configuration wherein the spines are arranged generally along a longitudinal axis of the catheter body.

14 Claims, 4 Drawing Sheets

(56) References Cited

U.S. PATENT DOCUMENTS

| | | | |
|---|---|---|---|
| 6,064,905 A | 5/2000 | Webster et al. | |
| 6,748,255 B2 | 6/2004 | Fuimaono et al. | |
| 6,973,340 B2 | 12/2005 | Fuimaono et al. | |
| 7,344,533 B2* | 3/2008 | Pearson | A61B 18/1477 606/41 |
| 7,377,906 B2 | 5/2008 | Selkee | |
| 7,850,685 B2* | 12/2010 | Kunis | A61B 18/1492 606/41 |
| 8,137,308 B2 | 3/2012 | Schultz | |
| 8,348,940 B2* | 1/2013 | Behl | A61B 18/1477 606/41 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0080409 A1 | 4/2005 | Young et al. | |
| 2012/0271302 A1 | 10/2012 | Behl et al. | |
| 2013/0103027 A1 | 4/2013 | Sklar et al. | |
| 2014/0194716 A1* | 7/2014 | Diep | A61B 5/6859 600/374 |
| 2015/0057519 A1 | 2/2015 | Ben-David et al. | |
| 2015/0105645 A1* | 4/2015 | Subramaniam | A61B 5/6859 600/374 |
| 2015/0141987 A1 | 5/2015 | Caplan et al. | |

OTHER PUBLICATIONS

U.S. Appl. No. 14/063,477.
European Search Report in corresponding European Patent Application No. EP 16188492.9, dated Feb. 9, 2017, pp. 1-8.
European Search Report from corresponding European Patent Application No. 16202848.4, dated May 8, 2017, pp. 1-8.
European Search Report from corresponding European Patent Application No. 16202870.8, dated May 10, 2017, pp. 1-8.
European Search Report from corresponding European Patent Application No. 16202871.6, dated May 10, 2017, pp. 1-8.

* cited by examiner

DUAL MULTIRAY ELECTRODE CATHETER

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. For example, catheters having basket-shaped electrode arrays are known and described, for example, in U.S. Pat. Nos. 5,772,590, 6,748,255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

It is desirable that a basket assembly be capable of detecting in as few beats as possible, including a single beat, as much of the electrical function of the region in which the electrode assembly is deployed, such as the left or right atrium. Conventional basket-shaped electrode assemblies are generally spherical or otherwise describe a smoothly rounded compact volume in which the spines, and correspondingly the electrodes, are constrained to the outer surface of the shape. However, the heart chamber or other region in which the catheter is deployed may not match the shape of the basket-shaped electrode assembly, resulting in a suboptimal degree of contact between one or more of the electrodes carried by the spines and the tissue being investigated.

Accordingly, it would be desirable to provide an EP mapping catheter that offers increased contact with an irregularly shaped heart chamber or other body cavity. As such, it would be desirable to provide such a catheter with spines having a greater degree of freedom than the spines of a conventional basket-shaped electrode assembly to allow them to more readily conform to surrounding walls of tissue. The techniques of this disclosure as described in the following materials satisfy these and other needs.

SUMMARY

The present disclosure is directed to a catheter with an elongated catheter body having proximal and distal ends and a dual multiray electrode assembly at the distal end of the catheter body, wherein the dual multiray electrode assembly includes a proximal multiray array and a distal multiray array, each array comprising a plurality of spines connected at one end and each spine comprising a plurality of electrodes and wherein the dual multiray electrode assembly has an expanded configuration and a collapsed configuration wherein the spines are arranged generally along a longitudinal axis of the catheter body.

In one aspect, the spines may curve radially outwardly in the expanded configuration. The spines of the proximal multiray array and the distal multiray array curve the same or opposite directions. For example, the spines of the proximal multiray array may curve proximally and the spines of the distal multiray array may curve distally or the spines of the proximal multiray array may curve distally and the spines of the distal multiray array may curve proximally.

In one aspect, the elongated catheter body may have an inner tubular member slidably disposed within a lumen of an outer tubular member, such that the proximal multiray array may be secured to a distal end of the outer tubular member and the distal multiray array may be secured to a distal end of the inner tubular member. Longitudinal movement of the inner tubular member and the outer tubular member may adjust a distance between the proximal multiray array and the distal multiray array.

In one aspect, the elongated catheter body may be deflectable.

In one aspect, each spine may be formed from a shape memory material.

This disclosure also includes a method for mapping a cavity of the body. A catheter having an elongated catheter body with proximal and distal ends and a dual multiray electrode assembly at the distal end of the catheter body, wherein the dual multiray electrode assembly comprises a proximal multiray array and a distal multiray array, each array comprising a plurality of spines connected at one end and each spine comprising a plurality of electrodes may be provided. Correspondingly, the distal end of the catheter may be introduced into the cavity, the dual multiray electrode assembly may be expanded from a collapsed configuration wherein the spines are arranged generally along a longitudinal axis of the catheter body to an expanded configuration, the dual multiray electrode assembly may be positioned within the cavity so that at least a portion of the electrodes are in contact with tissue forming the cavity and electrical data received from the at least a portion of the electrodes in contact with the tissue may be recorded.

In one aspect, the cavity of the body may be an atrium of the heart.

In one aspect, positioning the dual multiray electrode assembly within the chamber may include adjusting a relative distance between the proximal multiray array and the distal multiray array. Adjusting the relative distance between the proximal multiray array and the distal multiray array may cause the proximal multiray array and the distal multiray array to contact opposing walls of the cavity.

In one aspect, positioning the dual multiray electrode assembly within the chamber may include deflecting the elongated catheter body.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a dual multiray electrode assembly may conform more closely to the anatomy of the patient's heart in order to accurately map this electrical activity.

Figure 1:
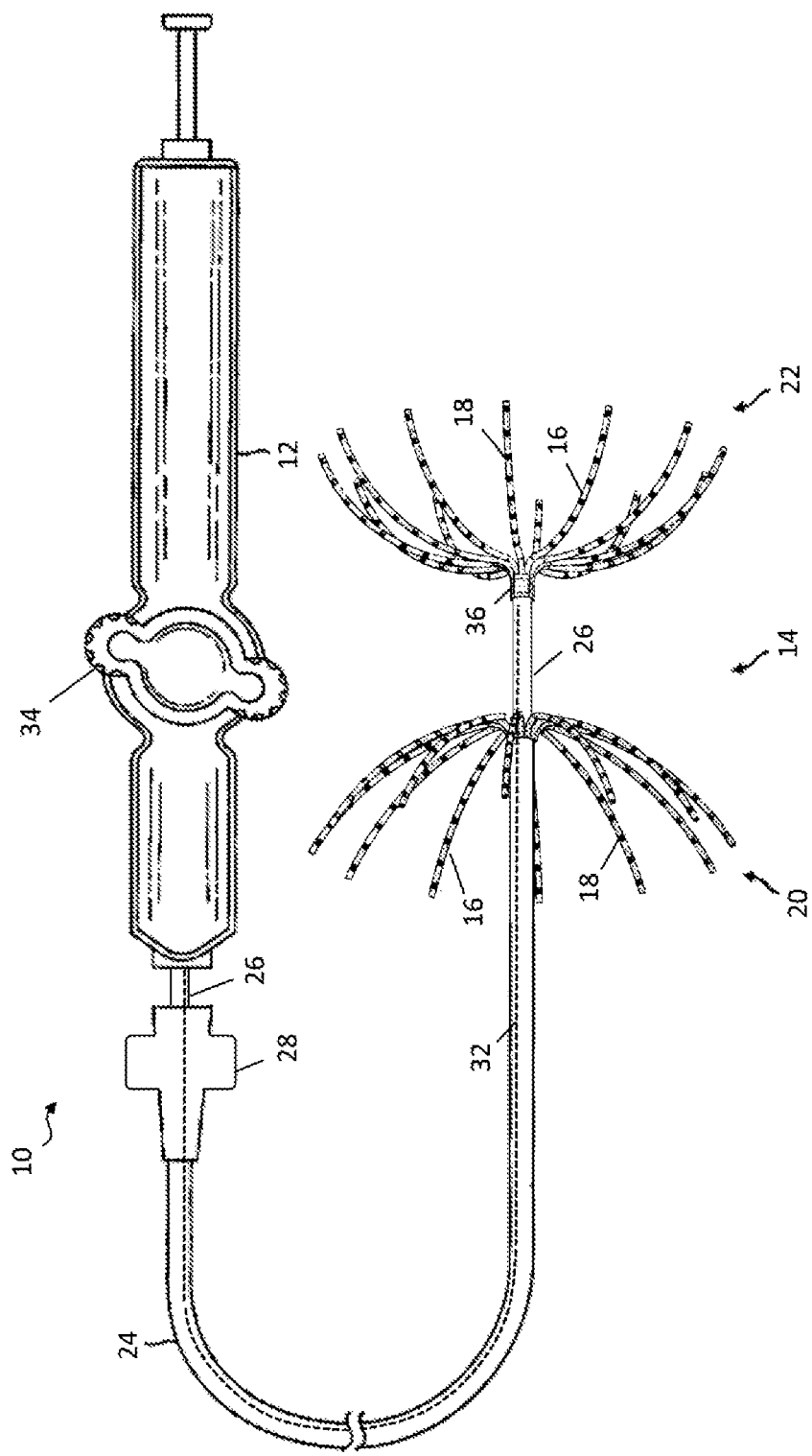
FIG. 1 is a top plan view of a catheter of the present invention, with a dual multiray electrode assembly in an expanded configuration, according to one embodiment.

As shown in FIG. 1, the catheter 10 has a proximal end with a control handle 12 and a distal end with a dual multiray electrode assembly 14 having a plurality of spines 16, each carrying multiple electrodes 18. Dual multiray electrode assembly 14 may include a proximal multiray array 20 and a distal multiray array 22. To enable adjustment in the relative distance between proximal multiray array 20 and distal multiray array 22, proximal multiray array 20 may be secured to the distal end of an outer tubular member 24 that is slidably disposed over inner tubular member 26. Control handle 12 may be secured to inner tubular member 26 and an actuator 28 may be secured to the proximal end of outer tubular member 24, so that by manipulating control handle 12 and actuator 28 to slide longitudinally relative to each other, an electrophysiologist may control the distance between proximal multiray array 20 and distal multiray array 22 at the distal end of catheter 10.

Inner tubular member 26 and outer tubular member 24 may constitute the catheter body and each may feature an elongated construction with a single, axial or central lumen, but can optionally have multiple lumens if desired. In particular, outer tubular member 24 may have a central lumen within which inner tubular member is coaxially disposed. Inner tubular member 26 may also feature one or more lumens for any suitable purpose, such as to deliver irrigation fluid. To enable accurate mapping of electrical signals, for example to detect most or substantially all of the electrical function of the right or left atrium in as little as a single heartbeat, it may be desirable to provide dual multiray electrode assembly 14 with a relatively high density of electrodes 18. As such, the numbers of spines 16 employed may be in the range of approximately 5 to 12 or any other suitable number. Spines 16 may be evenly or unevenly distributed radially. Further, each spine 16 may include multiple electrodes 18, such as in the range of approximately 5 to 30 electrodes per spine, although other numbers of electrodes may be employed. Similarly, the electrodes may be evenly distributed along the spine or may be skewed proximally, centrally or distally to facilitate analysis of the measured electrical signals.

Inner tubular member 26 and outer tubular members 24 are flexible, i.e., bendable, but substantially non-compressible along their lengths. The tubular members may be of any suitable construction and made of any suitable material. One construction comprises an outer wall made of polyurethane or PEBAX® (polyether block amide). The outer wall comprises an imbedded braided mesh of stainless steel or the like to increase torsional stiffness, so that rotation of a proximal end is translated into a corresponding rotation of the distal end, to facilitate guiding and positioning of dual multiray electrode assembly 14. The outer diameter of outer tubular member 24 is not critical, but generally should be as small as possible and may be no more than about 10 french depending on the desired application. Likewise the thicknesses of the outer walls of the tubular members is not critical, but may be thin enough so that interior lumens can accommodate a puller wire, lead wires, sensor cables and any other wires, cables or tubes. If desired, the inner surface of one or both outer walls may be lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In one aspect, spines 16 may include a material, such as a shape memory material as described below, that facilitates assuming an expanded arrangement to bring electrodes 18 into contact or closer proximity with tissue lining the walls of the cavity in which dual multiray electrode assembly 14 is deployed. Notably, as shown in FIG. 1, in one embodiment spines 16 of proximal multiray array 20 may have a preshaped configuration in which they form an arc curving in the proximal direction. Further, spines 16 of distal multiray array 22 may be preshaped to curve in the distal direction. As will be appreciated, the resiliency associated with the preshaped configurations may facilitate bringing electrodes 16 into contact with the surrounding tissue. Spines 16 may be sized appropriately depending on the patient's anatomy to provide a close fit to the area of the patient being investigated, such as the right or left atria.

Figure 2:
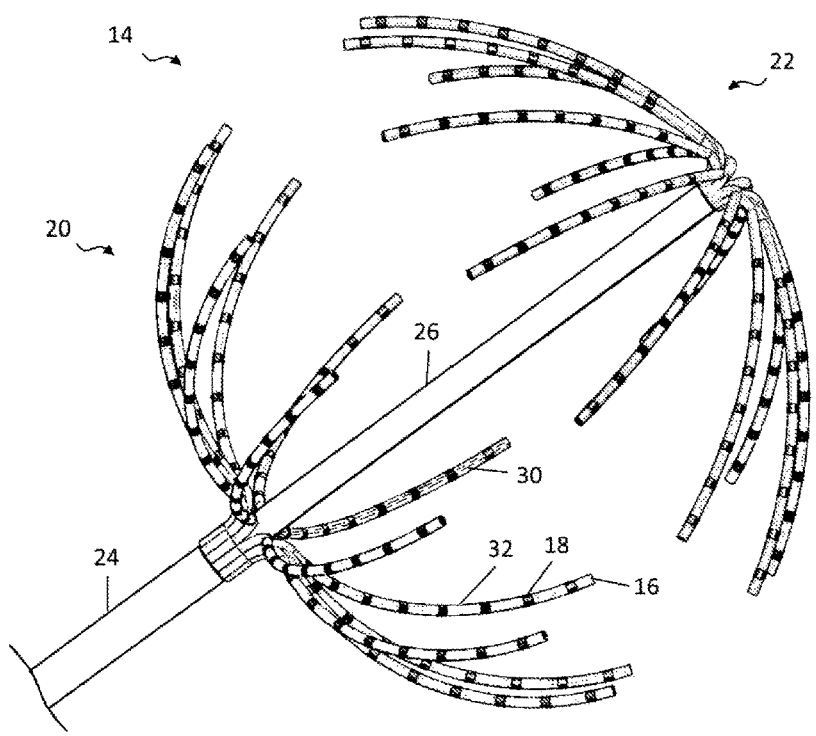
FIG. 2 is a schematic view of a dual multiray electrode assembly having a different expanded configuration, according to one embodiment.

A similar embodiment of dual multiray electrode assembly 14 is shown in more detail in FIG. 2. Here, spines 16 of proximal multiray array 20 may be preshaped to curve in the distal direction and spines 16 of distal multiray array 22 may be preshaped to curve in the proximal direction. Although this configuration resembles more conventional basket-shaped electrode assemblies, each spine 16 is secured at only one end, rather than at both proximal and distal ends. Like the embodiment shown in FIG. 1, this affords spines 16 a greater degree of freedom to conform to the surrounding tissue and may improve electrode contact. Also, the relative distance between proximal multiray array 20 and distal multiray array 22 by moving outer tubular member 24 relative to inner tubular member as described above. As such, the overall size of the area covered by electrodes 18 may adjusted. In contrast, a conventional basket-shaped electrode assembly may be expanded to different degrees, but does not offer this range of adjustment. In further embodiments, the spines 16 of both proximal multiray array 20 and distal multiray array 22 may be preshaped to curve in the same direction, either proximally or distally. Still further, in other embodiments, spines 16 may have any suitable preshaped configuration, including without limitation substantially straight at desired angles with respect to the longitudinal axis of catheter 10 and S-shaped.

Further details regarding one suitable construction of spines 16 are shown in FIG. 2 as well. Each spine 16 may comprise a flexible wire 30 (shown in phantom) with a non-conductive covering 32 on which one or more of the ring electrodes 18 are mounted. In an embodiment, the flexible wires 30 may be formed from a shape memory material to facilitate the transition between expanded and collapsed arrangements and the non-conductive coverings 32 may each comprise a biocompatible plastic tubing, such as polyurethane or polyimide tubing. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the dual multiray electrode assembly 14 may have a three dimensional shape that can be easily collapsed to be fed into a guiding sheath and then readily returned to its expanded shape memory configuration upon delivery to the desired region of the patient upon removal of the guiding sheath.

Alternatively, in some embodiments the spines 16 can be designed without the internal flexible wire 30 if a sufficiently rigid nonconductive material is used for the non-conductive covering 32 to permit radial expansion of the dual multiray electrode assembly 14, so long as the spine has an outer surface that is non-conductive over at least a part of its surface for mounting of the ring electrodes 18.

Figure 3:
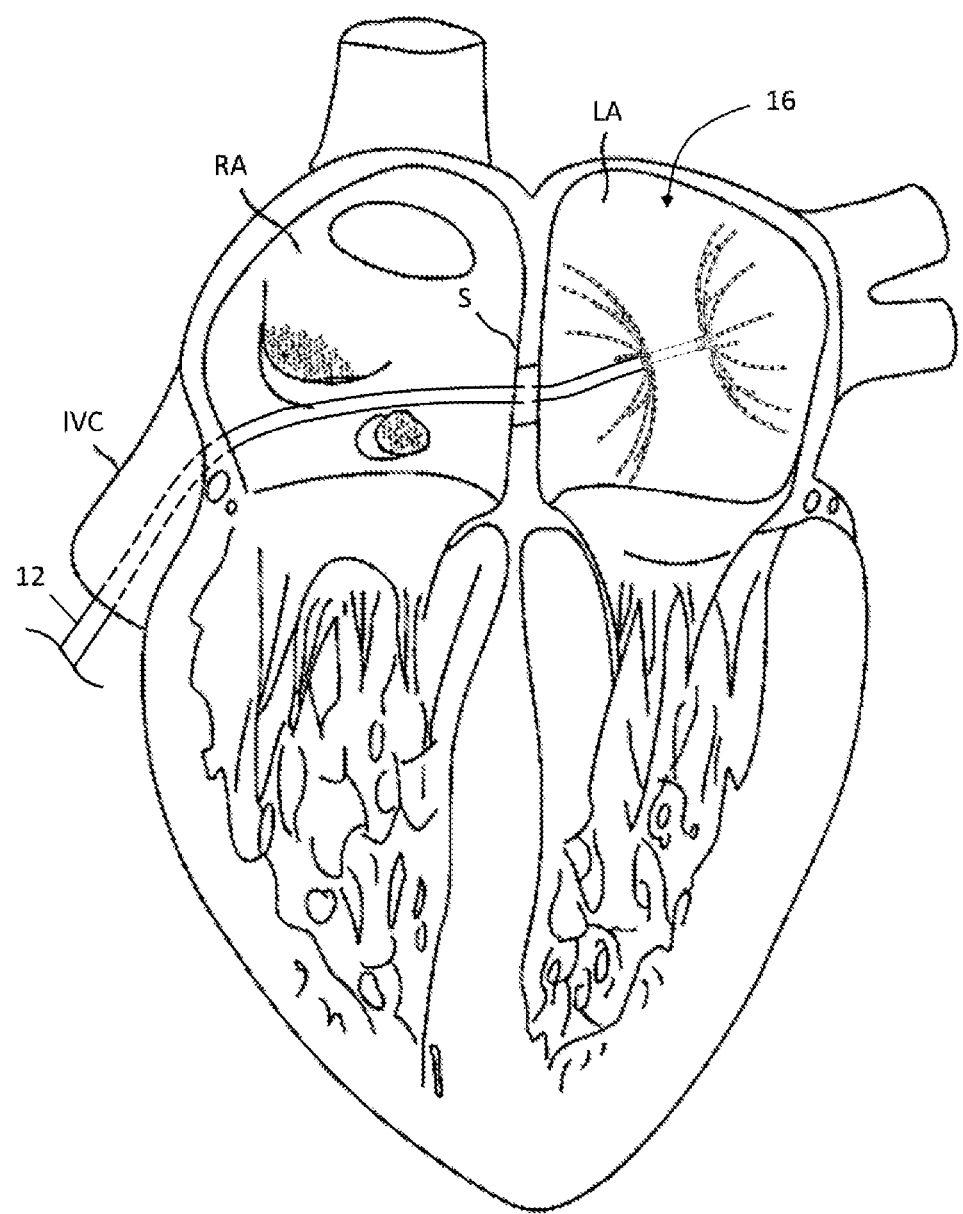
FIG. 3 is a schematic view of a dual multiray electrode within the left atrium, according to one embodiment.

In one aspect, an electrophysiologist may introduce a guiding sheath, guidewire and dilator into the patient, as is generally known in the art. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the expander permits the catheter to pass over the guidewire. In one exemplary procedure as depicted in FIG. 3, the catheter is first introduced to the right atrium (RA) via the inferior vena cava (IVC), where it passes through the septum (S) in order to reach the left atrium (LA).

As will be appreciated, the guiding sheath covers the spines 16 of the dual multiray electrode assembly 14 in a collapsed position so that the entire catheter can be passed through the patient's vasculature to the desired location. The expander 22 may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the dual multiray electrode assembly 14. Once the guiding sheath is withdrawn, spines 16 flex outwardly and attempt to assume their preshaped expanded configuration. With the dual multiray electrode assembly 14 radially expanded, the ring electrodes 18 contact atrial tissue. Aspects of the configuration of dual multiray electrode assembly 14 may be tailored to more closely conform to the area in which it is deployed.

In one aspect, outer tubular member 24 may be withdrawn proximally, such as by manipulation of actuator 28, to impart a desired degree of contact between the electrodes 18 of proximal multiray array 20 into contact with the septum wall. Further, inner tubular member 26 may be advanced distally, such as by manipulation of control handle 12, to bring distal multiray array 22 into contact with the opposing wall. These techniques may be adapted for any cavity in which dual multiray electrode assembly 14 may be deployed and used to adjust dual multiray electrode assembly 14 to the size of the cavity. When the dual multiray electrode assembly 14 is expanded, and the relative distance between proximal multiray array 20 and distal multiray array 22 adjusted if desired, the electrophysiologist may map local activation time and/or ablate using electrodes 18, which can guide the electrophysiologist in diagnosing and providing therapy to the patient. The catheter may include one or more reference ring electrodes mounted on the catheter body and/or one or more reference electrodes may be placed outside the body of the patient. By using the inventive catheter with the multiple electrodes on the dual multiray electrode assembly, the electrophysiologist can obtain a true anatomy of a cavernous region of the heart, including an atrium, by measuring less points than with traditional catheters, allowing a more rapid mapping of the region.

In a further aspect, each spine 16 may include cabling with built-in or embedded lead wires for the electrodes 18 carried by the spine as described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which are hereby incorporated by reference.

Figure 4:
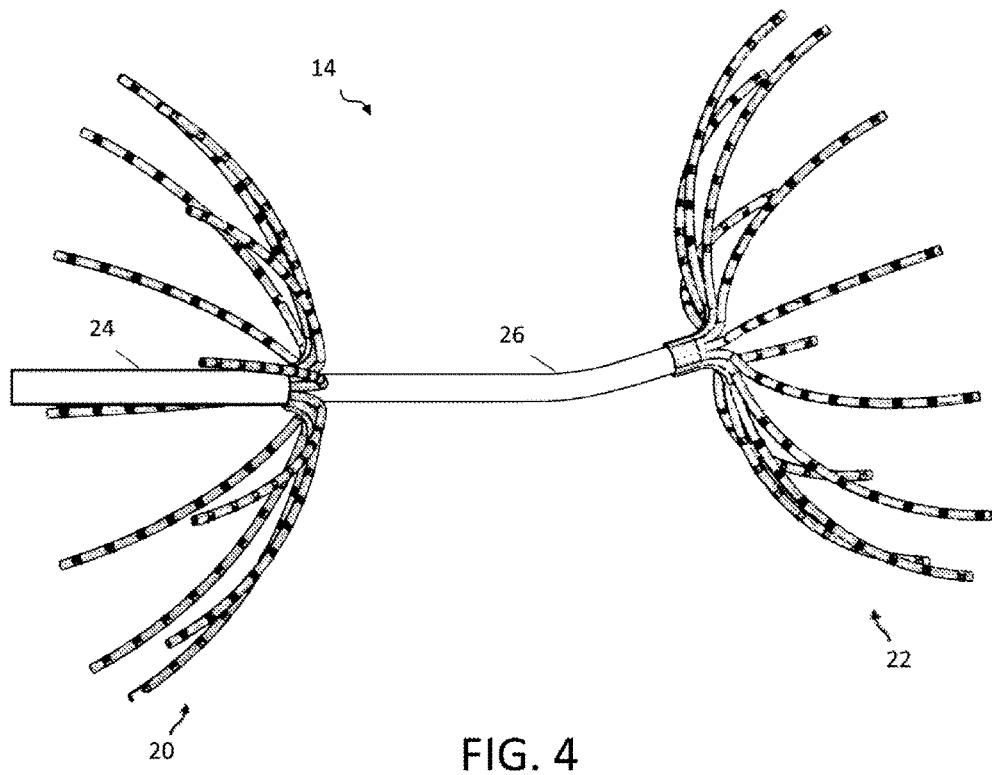
FIG. 4 is a schematic view of a dual multiray electrode assembly that is deflected, according to one embodiment.

Returning to FIG. 1, dual multiray electrode assembly 14 may include a deflectable portion to impart further control over which areas of tissue are contacted in some embodiments. At least one puller wire 32 may be secured at its distal end to a distal portion of inner tubular member 26 and at its proximal end to a deflection arm 34 on control handle 12. Rotating deflection arm 34 places puller wire 32 under tension, producing a deflection of inner tubular member 26. One puller wire may be employed to impart a uni-directional deflection, while an additional puller wire may provide bi-directional deflection. Examples of suitable construction details for deflectable catheters for are described in U.S. Pat. No. 7,377,906, entitled STEERING MECHANISM FOR BI-DIRECTIONAL CATHETER, and U.S. Pat. No. 8,137,308, entitled CATHETER WITH ADJUSTABLE DEFLECTION SENSITIVITY, the entire disclosures of which are hereby incorporated by reference. FIG. 4 illustrates the deflection of distal multiray array 22 of dual multiray electrode assembly 14. Alternatively or in addition, outer tubular member 24 may also be deflectable as desired using similar techniques.

Figure 5:
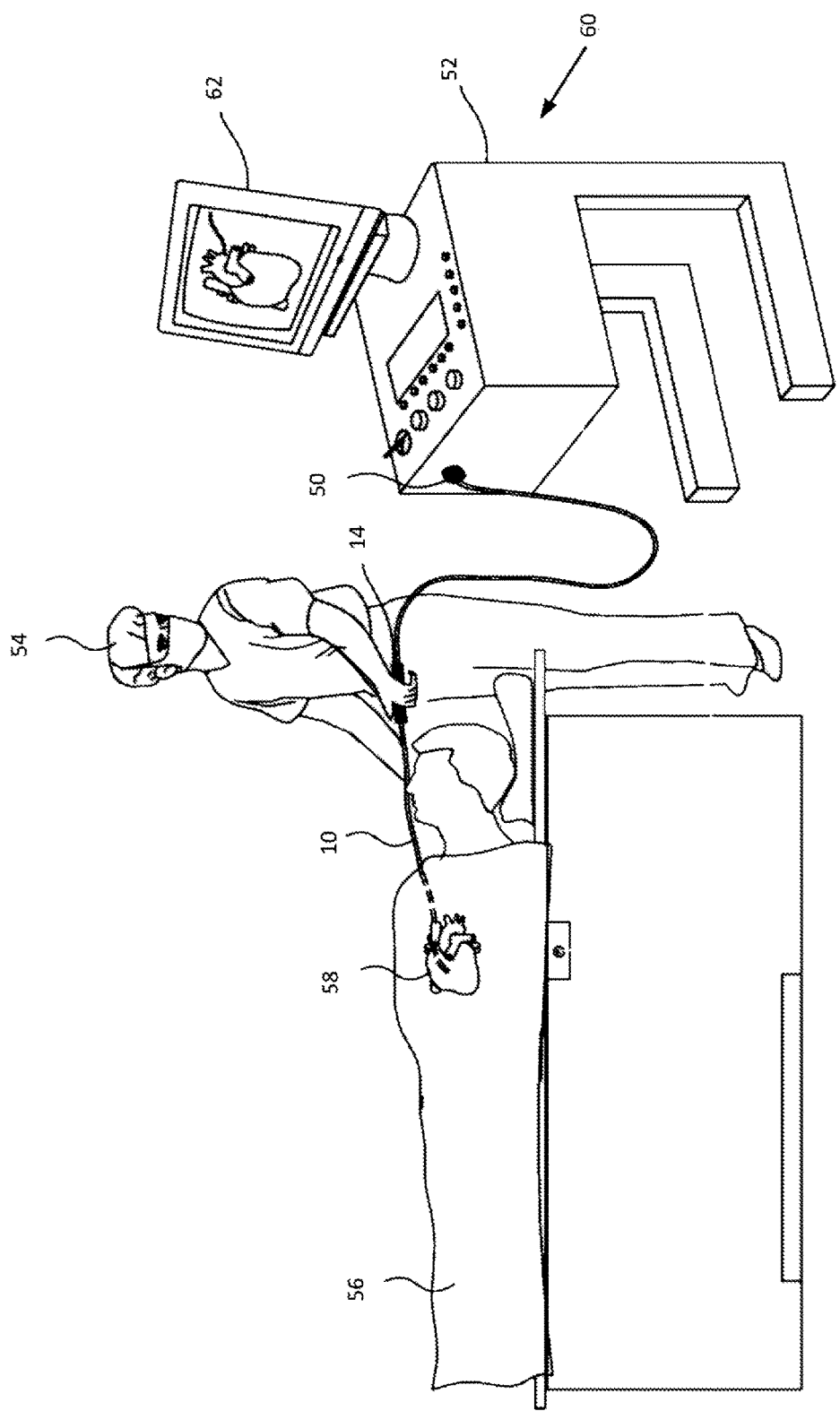
FIG. 5 is a schematic illustration of an invasive medical procedure using a dual multiray electrode assembly, according to one embodiment.

To help illustrate use of the dual multiray electrode assembly 14, FIG. 5 is a schematic depiction of an invasive medical procedure, according to an embodiment of the present invention. Catheter 10, with the dual multiray electrode assembly 14 (not shown in this view) at the distal end may have a connector 50 at the proximal end for coupling the wires from their respective electrodes 18 (not shown in this view) to a console 52 for recording and analyzing the signals they detect. An electrophysiologist 54 may insert the catheter 10 into a patient 56 in order to acquire electropotential signals from the heart 58 of the patient. The professional uses the control handle 14 attached to the catheter in order to perform the insertion. Console 52 may include a processing unit 60 which analyzes the received signals, and which may present results of the analysis on a display 62 attached to the console. The results are typically in the form of a map, numerical displays, and/or graphs derived from the signals.

In a further aspect, the processing unit 60 may also receive signals from one or more location sensors 36 provided near a distal end of the catheter 10 adjacent the dual multiray electrode assembly 14 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 60 to determine the position, (e.g., the location and orientation) of the distal end of catheter 10 within the heart cavity. The electrophysiologist may then view the position of the dual multiray electrode assembly 14 on an image the patient's heart on the display 62. By way of example, this method of position sensing may be implemented using the CARTO™ system, produced by Biosense Webster Inc. (Diamond Bar, Calif.) and is described in detail in U.S. Pat. Nos. 5,391,199; 6,690,963; 6,484,118; 6,239,724; 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the dual multiray electrode assembly 14. The coordinates of the distal sensor relative to the proximal sensor may be determined and, with other known information pertaining to the curvature of the spines 16 of the dual multiray electrode assembly 14, used to find the positions of each of the electrodes 18.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and a dual multiray electrode assembly at the distal end of the catheter body, wherein the dual multiray electrode assembly comprises a proximal multiray array and a distal multiray array, each array comprising a plurality of spines connected at one end and each spine comprising a plurality of electrodes, and wherein the dual multiray electrode assembly has an expanded configuration and a collapsed configuration wherein the spines are arranged generally along a longitudinal axis of the catheter body, the elongated catheter body comprising an inner tubular member connected at a proximal end to a control handle and an outer tubular member being secured to an actuator, the inner tubular member being slidably disposed within a lumen of the outer tubular member, the proximal multiray array being secured to a distal end of the outer tubular member and the distal multiray array being secured to a distal end of the inner tubular member.

2. The catheter of claim 1, wherein the spines curve radially outwardly in the expanded configuration.

3. The catheter of claim 2, wherein the spines of the proximal multiray array and the distal multiray array curve in opposite directions.

4. The catheter of claim 3, wherein the spines of the proximal multiray array curve proximally and the spines of the distal multiray array curve distally.

5. The catheter of claim 3, wherein the spines of the proximal multiray array curve distally and the spines of the distal multiray array curve proximally.

6. The catheter of claim 2, wherein the spines of the proximal multiray array and the distal multiray array curve in a same direction.

7. The catheter of claim 1, wherein relative longitudinal movement of the inner tubular member and the outer tubular member adjusts a distance between the proximal multiray array and the distal multiray array.

8. The catheter of claim 1, wherein the elongated catheter body comprises a deflection arm.

9. The catheter of claim 1, wherein each spine comprises a shape memory material.

10. A method for mapping a cavity of the body comprising:
providing a catheter having an elongated catheter body with proximal and distal ends and a dual multiray electrode assembly at the distal end of the catheter body, wherein the dual multiray electrode assembly comprises a proximal multiray array and a distal multiray array, each array comprising a plurality of spines connected at one end and each spine comprising a plurality of electrodes, the elongated catheter body comprising an inner tubular member connected at a proximal end to a control handle and an outer tubular member being secured to an actuator, the inner tubular member being slidably disposed within a lumen of the outer tubular member, the proximal multiray array being secured to a distal end of the outer tubular member and the distal multiray array being secured to a distal end of the inner tubular member;
introducing the distal end of the catheter into the cavity;
expanding the dual multiray electrode assembly from a collapsed configuration wherein the spines are arranged generally along a longitudinal axis of the catheter body to an expanded configuration;
positioning the dual multiray electrode assembly within the cavity so that at least a portion of the electrodes are in contact with tissue forming the cavity; and
recording electrical data received from the at least a portion of the electrodes in contact with the tissue.

11. The method of claim 10, wherein the cavity of the body is an atrium of the heart.

12. The method of claim 10, wherein positioning the dual multiray electrode assembly within the cavity comprises adjusting a relative distance between the proximal multiray array and the distal multiray array.

13. The method of claim 12, wherein adjusting the relative distance between the proximal multiray array and the distal multiray array causes the proximal multiray array and the distal multiray array to contact opposing walls of the cavity.

14. The method of claim 10, wherein positioning the dual multiray electrode assembly within the cavity comprises deflecting the elongated catheter body.

* * * * *